United States Patent [19]

Ichikawa et al.

[11] Patent Number: 5,498,806
[45] Date of Patent: Mar. 12, 1996

[54] PROCESS FOR PREPARING 1-CHLORO-1,2,2-TRIFLUOROETHYLENE OR 1,2,2-TRIFLUOROETHYLENE

[75] Inventors: Masaru Ichikawa; Ryuichiro Ohnishi; Hisao Suzuki, all of Sapporo, Japan

[73] Assignee: Daikin Industries Ltd., Osaka, Japan

[21] Appl. No.: 369,259

[22] Filed: Jan. 5, 1995

Related U.S. Application Data

[63] Continuation of Ser. No. 74,153, Jun. 9, 1993, abandoned, which is a continuation of Ser. No. 938,682, Sep. 1, 1992, abandoned, which is a continuation of Ser. No. 707,031, May 29, 1991, abandoned.

[30] Foreign Application Priority Data

| | | | |
|---|---|---|---|
| May 31, 1990 | [JP] | Japan | 2-143053 |
| May 31, 1990 | [JP] | Japan | 2-143054 |
| Sep. 11, 1990 | [JP] | Japan | 2-241691 |
| Sep. 11, 1990 | [JP] | Japan | 2-241692 |

[51] Int. Cl.$^6$ .......................... C07C 17/25; C07C 21/18
[52] U.S. Cl. .......................... 570/156; 570/176
[58] Field of Search .................... 570/156, 176

[56] References Cited

U.S. PATENT DOCUMENTS 2,697,124  12/1954  Mantell ................................. 570/156

FOREIGN PATENT DOCUMENTS 0253410  1/1988  European Pat. Off. ............... 570/156

*Primary Examiner*—Alan Siegel
*Attorney, Agent, or Firm*—Birch, Stewart, Kolasch & Birch

[57] ABSTRACT

1-Chloro-1,2,2-trifluoroethylene or 1,2,2-trifluoroethylene is prepared by reacting 1,1,2-trichloro-1,2,2-trifluoroethane and hydrogen in the presence of a catalyst which comprises at least one metal selected from the group consisting of palladium, rhodium and ruthenium and at least one metal selected from the group consisting of mercury, lead, cadmium, tin, indium, copper, bismuth, thallium and silver and a carrier selected from the group consisting of $Al_2O_3$, $SiO_2$ and activated carbon, whereby selectivities and yields of 1-chloro-1,2,2-trifluoroethylene or 1,2,2-trifluoroethylene are optimized by selecting the kinds of metals and supports.

7 Claims, No Drawings

PROCESS FOR PREPARING 1-CHLORO-1,2,2-TRIFLUOROETHYLENE OR 1,2,2-TRIFLUOROETHYLENE

This application is a continuation of application Ser. No. 08/074,153 filed on Jun. 9, 1993, now abandoned which is a continuation of Ser. No. 07/938,682, filed on Sept. 1, 1992, now abandoned which is a continuation of Ser. No. 07/707,031, filed on May 29, 1991, now abandoned.

BACKGROUND OF THE INVENTION

1. Field of the Invention

The present invention relates to a process for preparing 1-chloro-1,2,2-trifluoroethylene or 1,2,2-trifluoroethylene in high selectivities and yields, which product is useful as a raw material for the preparation of polychlorotrifluoroethylene and substituted fluorohydrocarbons.

2. Description of the Related Art

Japanese Patent Publication No. 8454/1968 discloses a process for preparing 1,2,2-trifluoroethylene (hereinafter referred to as "3FH") by reacting 1,1,2-trichloro-1,2,2-trifluoroethane (hereinafter referred to as "R-113") and hydrogen at a temperature of 200° to 300° C. in the presence of a catalyst comprising palladium supported on activated carbon (Pd/carbon). By this process, 1-chloro-1,2,2-trifluoroethylene (hereinafter referred to as "3FCL") is obtained together with 3FH, but selectivities of other by-products are high and therefore the selectivity of 3FH and 3FCL is only 40 to 85%.

By a process of preparing a mixture of 3FH and 3FCL from R-113 and hydrogen in the presence of a platinum group metal supported on alkali magnesium fluoride as a catalyst which is disclosed in EP-A-063 657, 3FH and 3FCL there are obtained at a high selectivity of 90% or higher. But, the reaction temperature should be as high as 500° C. By conducting the reaction at a low temperature of 200° to 300° C. in the presence of the above catalyst containing 0.5% of palladium, the selectivity remains low.

For the preparation of 3FCL, various other processes are also known. One example is a non-catalytic process comprising dechlorination of R-113 with zinc in a liquid phase (cf. Japanese Patent Publication Nos. 45322/1972, 5207/1982 and 5208/1982), and another is a catalytic process comprising dechlorination of R-113 with hydrogen in a gas phase (cf. Japanese Patent Publication No. 26484/1972, Japanese Patent Kokai Publication Nos. 185734/1985, 61936/1987 and 29328/1989 and GB Patent No. 698,386).

By using the liquid phase non-catalytic process with zinc, a comparatively high yield is obtained, but the production of by-produced zinc chloride is troublesome. In addition, the liquid phase process should use an anhydrous organic solvent. Using the gas phase dechlorination proceedure, the satisfactory high selectivity is achieved only under reduced pressure (for example, a selectivity of 95% under 310 Torr. in Japanese Patent Kokai Publication No. 61936/1987 but at a high reaction temperature (for example, a selectivity of 82 to 95% at 500° C. in EP-A-053 657). The catalyst life is limited due to serious coke-poisoning.

SUMMARY OF THE INVENTION

One object of the present invention is to provide a process for preparing 3FH or 3FCL at a comparatively low temperature under atmospheric pressure.

Another object of the present invention is to provide a process for preparing 3FH and 3FCL, by which a ratio of prepared 3FH and 3FCL can be controlled.

According to the present invention, there is provided a process for preparing 3FCL and 3FH comprising reacting R-113 and hydrogen in the presence of a catalyst which comprises at least one metal selected from the group consisting of palladium, rhodium and ruthenium and at least one metal selected from the group consisting of mercury, lead, cadmium, tin, indium, copper, bismuth, thallium and silver and a carrier selected from the group consisting of $Al_2O_3$, $SiO_2$ and activated carbon.

The reactions which proceed in the process of the present invention are as follows:

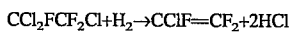

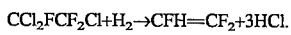

DETAILED DESCRIPTION OF THE INVENTION

In the present invention, the catalyst comprises at least one metal selected from the group consisting of palladium, rhodium and ruthenium (basic metals) and at least one metal selected from the group consisting of mercury, lead, cadmium, tin, indium, copper, bismuth, thallium and silver (additive metals), and a carrier selected from the group consisting of $Al_2O_3$, $SiO_2$ and activated carbon.

An amount of the basic metal to be supported on the carrier is from 0.1 to 10% by weight, preferably from 0.5 to 5% by weight.

The metal can be supported on the carrier by a per se conventional method. For example, the carrier material is dipped in a solution of a salt or a metal compound of the metal such as a nitrate, a carbonate, a sulfate, a halide (e.g. a chloride, a fluoride, etc.), a hydroxide, a phosphate, a perchlorate, an organic metal compound or a salt with an organic acid (e.g. acetates, acetylacetonates, carbonyls, etc.) Then, the solvent is removed, and the residue is subjected to calcination and reduction with hydrogen at 300 to 773K.

Two kinds of metals are simultaneously supported on the carrier, although they may be successively supported on the carrier.

A molar ratio of the additive metal to the basic metal may vary according to the kinds of the two metals, the intended selectivities of 3FCL and 3FH, and the like. The molar ratio of the additive metal to the basic metal is usually from 0.01:1 to 10:1, preferably from 0.2:1 to 4:1.

In case of bismuth, this molar ratio is at least 0.05:1 preferably at least 0.2:1, and in case of the metals other than bismuth, this molar ratio is at least 0.2:1, preferably at least 0.5:1. When this molar ratio is too large, the conversion decreases. Therefore, the maximum molar ratio is preferably 4:1.

For example, when a Hg/Pd ratio is less than 0.5, the selectivity of 3FH greatly decreases so that the overall selectivity of the olefins is decreased. When a Tl/Pd ratio is 4, 3FCL is obtained at a selectivity of 96% or higher. When the Tl/Pd ratio is 0.5, 3FH is predominantly produced.

According to the present invention, by the selection of the additive metal, a molar ratio of 3FCL to 3FH in the product can be changed. For example, when mercury, lead and copper are used as the additive metal, the molar ratio of 3FCL to 3FH is 0.11, 0.58 and 5.8, respectively.

A molar ratio of hydrogen to R-113 is preferably from 0.5 to 4.0, more preferably from 0.5 to 3.5. If this ratio is large, hydrogenated paraffin compounds are hardly produced and the high selectivity of 3FCL and 3FH is maintained. However, the molar ratio of larger than 4.0 is uneconomical. When the molar ratio is smaller than 0.5, the conversion decreases.

A W/F ratio corresponding to a contact time, in which W is an amount (g) of the catalyst and F is a total flow rate (ml/sec.) under the normal state, is in a range between 0.6 and 5.8. In this range, the selectivity is not influenced substantially, but the conversion is influenced. When this ratio is smaller than 0.6, the conversion is unacceptably small.

A reaction temperature is from 150° to 400° C., preferably from 200° to 350° C. In the temperature range between 200° C. and 350° C., 3FCL and 3FH are produced at a high selectivity of 87° to 100° C.

PREFERRED EMBODIMENTS OF THE INVENTION

The present invention will be illustrated by following Examples.

General procedures for supporting an additive metal on a carrier (I)

A suitable amount of a salt of an additive metal to be supported is dissolved in water (30 ml). In a solution, were added formalin (0.2 g) and a pellet form palladium catalyst of 3.2 mm in diameter and 3.2 mm in height comprising 0.5% of palladium carried on $Al_2O_3$ (5 g) (Catalyst A); a catalyst prepared by pulverizing said pellet form palladium catalyst to 60 mesh or lower (4 g) (Catalyst B); a powdery catalyst comprising 2% of palladium carried on activated carbon (1.5 g) (Catalyst C); or a powdery catalyst comprising 5% of a basic metal carried on $Al_2O_3$ (4 g) (Catalyst D). All of the catalysts are commercially available from N. E. CHEMICAL CATALYST. Then, the mixture was aged at 50° C. for 2 to 3 hours. An amount of the additive metal is adjusted to obtain an intended molar ratio of the additive metal to the basic metal.

Then, water is removed by a rotary evaporator and the residue is dried in air at 100° C. for 12 hours.

Each of the produced Catalysts A, B and C is pretreated in a hydrogen stream at a temperature of 300° to 400° C. for 2 hours. When bismuth is used, the catalyst is pretreated in an oxygen stream at 300° C. for 2 hours.

EXAMPLE 1

$HgCl_2$, as the additive metal salt, was used in such an amount that the molar ratio of Hg to Pd in the catalyst was 4:1.

In a Hastelloy C made tube reactor having an inner diameter of 20 mm, Catalyst A (4 g) modified with $HgCl_2$ as above was charged, and through the reactor tube, a mixture of R-113 and hydrogen in a molar ratio of 1:2 was flowed at a total flow rate of 21 ml/min. at 200° C.

A conversion was 17.2%, and selectivities of 3FCL and 3FH were 24.6% and 75.4%, respectively.

EXAMPLE 2

In the same manner as in Example 1 but using $Pb(NO_3)_3$ as the additive metal salt, adjusting the Pb/Pd molar ratio to 4:1 and keeping the reaction temperature at 280° C., the reaction was carried out.

A conversion was 46.8%, and selectivities of 3FCL, 3FH, R-123a ($CHClFCClF_2$), R-141a ($CHCl_2CH_2F$), R-160 ($CH_2ClCH_3$) and R-142 ($CHF_2CH_2Cl$) were 23.4%, 71.0%, 2.7%, 1.1%, 0.6% and 0.3%, respectively.

EXAMPLE 3

In the same manner as in Example 1 but using $CdCl_2$ as the additive metal salt, adjusting the Cd/Pd molar ratio to 4:1 and keeping the reaction temperature at 280° C., the reaction was carried out.

A conversion was 21.6%, and selectivities of 3FCL, 3FH, R-160, R-123a, R-142 and R-141a were 33.4%, 58.8%, 2.0%, 1.9%, 1.6% and 1.5%, respectively.

EXAMPLE 4

In the same manner as in Example 1 but using $SnCl_2$ as the additive metal salt, adjusting the Sn/Pd molar ratio to 4:1 and keeping the reaction temperature at 250° C., the reaction was carried out.

A conversion was 15.9%, and selectivities of 3FCL, 3FH and R-142 were 79.3%, 15.3% and 2.5%, respectively.

EXAMPLE 5

In the same manner as in Example 1 but using $InCl_3$ as the additive metal salt, adjusting the In/Pd molar ratio to 4:1 and keeping the reaction temperature at 250° C., the reaction was carried out.

A conversion was 10.4%, and selectivities of 3FCL, 3FH, R-142, R-160, R-123a and R-141a were 71.9%, 16.1% 4.6%, 2.9%, 2.3% and 1.3%, respectively.

EXAMPLE 6

In the same manner as in Example 1 but using $CuCl_2$ as the additive metal salt, adjusting the Cu/Pd molar ratio to 4:1 and keeping the reaction temperature at 250° C., the reaction was carried out.

A conversion was 18.7%, and selectivities of 3FCL, 3FH and R-142 were 79.5%, 17.2% and 1.9%, respectively.

EXAMPLE 7

$AgNO_3$, as the additive metal salt, was used in such an amount that the molar ratio of Ag to Pd in the catalyst was 4:1.

In a stainless steel made tube reactor having an inner diameter of 7.2 mm, Catalyst B (1.3 g) modified with $AgNO_3$ as above was charged, and through the reactor tube, a mixture of R-113 and hydrogen in a molar ratio of 1:2 was flowed at a total flow rate of 27 ml/min. at 250° C.

A conversion was 32.2%, and selectivities of 3FH, 3FCL, R-142, R-123a, R-160 and R-141a were 29.3%, 67.0%, 1.2%, 0.9%, 0.5% and 0.3%, respectively.

EXAMPLE 8

In the same manner as in Example 7 but using $HgCl_2$ as the additive metal salt and flowing a mixture of hydrogen and R-113 at a total flow rate of 60 ml/min., the reaction was carried out.

A conversion was 54.7%, and selectivities of 3FCL, 3FH, R-152a ($CF_2HCH_3$), R-123a and R-142 were 9.3%, 87.4%, 2.2%, 0.7% and 0.4%, respectively.

EXAMPLE 9

In the same manner as in Example 8 but flowing the mixture of hydrogen and R-113 at a total flow rate of 27 ml/min., the reaction was carried out.

A conversion was 45.2%, and selectivities of 3FH, 3FCL, R-123a, R-152a, R-142 and R-160 were 82.7%, 7.6%, 4.8%, 1.5%, 0.6% and 0.5%, respectively.

EXAMPLE 10

In the same manner as in Example 8 but flowing a mixture of R-113 and hydrogen in a molar ratio of 1:4, the reaction was carried out.

A conversion was 40.0%, and selectivities of 3FH, 3FCL, R-123a, R-141a, R-152a, R-142 and R-160 were 76.9%, 12.0%, 5.8%, 2.1%, 1.7%, 0.7 and 0.5%, respectively.

EXAMPLE 11

In the same manner as in Example 7 but using $Pb(NO_3)_3$ as the additive metal salt, adjusting the Pb/Pd molar ratio to 4:1 and flowing a mixture of R-113 and hydrogen in a molar ratio of 1:1 at a total flow rate of 18 ml/min., the reaction was carried out.

A conversion was 11.2%, and selectivities of 3FH, 3FCL, R-123a, R-152a and R-142 were 60.4%, 35.1%, 2.1%, 1.0% and 0.9%, respectively.

EXAMPLE 12

In the same manner as in Example 11 but using a mixture of R-113 and hydrogen in a molar ratio of 1:4, the reaction was carried out.

A conversion was 12.0%, and selectivities of 3FH and 3FCL were 56.3% and 43.7%, respectively.

EXAMPLE 13

In the same manner as in Example 12 but keeping the reaction temperature at 300° C. the reaction was carried out.

A conversion was 22.9%, and selectivities of 3FH, 3FCL, R-123a, R-142 and R-152a were 44.3%, 49.4%, 1.9%, 1.4% and 1.4%, respectively.

EXAMPLE 14

In the same manner as in Example 9 but using Catalyst D (1.3 g) comprising palladium as the base metal and modified with $HgCl_2$ in the Hg/Pd molar ratio of 1:1, the reaction was carried out.

A conversion was 60.8%, and selectivities of 3FCL, 3FH, R-123a, R-134a ($CF_3CFH_2$), R-141a, R-142 and R-160 were 79.0%, 12.1%, 3.6%, 2.4%, 1.5%, 0.6% and 0.5%, respectively.

Comparative Example 1

In the same manner as in Example 8 but using Catalyst C (0.6 g) modified with the said amount of $HgCl_2$ and keeping the reaction temperature at 280° C., the reaction was carried out.

A conversion was 63.9%, and selectivities of 3FH, 3FCL and R-123a were 16.0%, 62.2% and 21.9%, respectively.

Comparative Example 2

In the same manner as in Example 1 but using Catalyst C (0.6 g) modified with $Pb(NO_3)_3$ as the additive metal salt in the Pb/Pd molar ratio of 4:1 and keeping the reaction temperature at 280° C., the reaction was carried out.

A conversion was 28.5%, and selectivities of 3FH, 3FCL and R-123a were 6.0%, 69.2% and 24.8%, respectively.

Comparative Example 3

In the same manner as in Example 8 but using no metal other than palladium, the reaction was carried out.

A conversion was 64.3%, and selectivities of 3FCL, 3FH, R-143, R-141a, R-123a, R-142, R-160 and R-152a were 0%, 23.0%, 40.2%, 18.7%, 7.0%, 6.0%, 4.6% and 0.7%, respectively.

Comparative Example 4

In the same manner as in Examples 1 to 7 but using no metal other than palladium and keeping the reaction temperature at 150° C., the reaction was carried out.

A conversion was 24.7%, and selectivities of 3FH, R-143, R-141a, R-160, R-142 and R-123a were 1.5%, 44.2%, 41.2%, 1.0%, 3.7% and 8.5%, respectively.

EXAMPLE 15

As the additive metal salt, $BiCl_3$ was used in such an amount that the molar ratio of Bi to Pd in the catalyst was 0.4:1.

In a glass tube reactor having an inner diameter of 10 mm, Catalyst D comprising palladium as the base metal and modified with $BiCl_3$ as above was charged, and through the reactor tube, a mixture of R-113 and hydrogen in a molar ratio of 1:3 was flowed at a total flow rate of 31 ml/min. at 250° C.

A conversion was 96.4%, and selectivities of 3FH, 3FCL, R-152a and R-123a were 81.3%, 8.9%, 6.1% and 1.3%, respectively.

EXAMPLE 16

In a glass tube reactor having an inner diameter of 10 mm, Catalyst D (1 g) comprising ruthenium as the base metal and modified with $TlNO_3$ in the molar ratio of Tl/Rh of 2:1 was charged, and through the reactor tube, a mixture of R-113 and hydrogen in a molar ratio of 3:4 was flowed at a total flow rate of 35 ml/min. at 230° C.

A conversion was 4.5%, and selectivities of 3FCL, 3FH, R-143a and R-123a were 71.8%, 19.3%, 2.6% and 2.3%, respectively.

Comparative Example 5

In the same manner as in Example 16 but using no thallium, the reaction was carried out.

A conversion was 12.5%, and selectivities of 3FCL, 3FH, R-143, R-141a, R-123a and ethane were 26.7%, 3.7%, 22.0%, 21.8%, 9.0% and 6.6%, respectively.

EXAMPLE 17

In a glass tube reactor having an inner diameter of 10 mm, Catalyst D (1 g) comprising ruthenium as the base metal and modified with $HgCl_2$ in a molar ratio of 1:1 (1 g) was charged, and through the reactor tube, a mixture of R-113 and hydrogen in a molar ratio of 1:2 was flowed at a total flow rate of 30 ml/min. at 200° C.

A conversion was 18 7%, and selectivities of 3FCL, 3FH and R-1132a ($CF_2CH_2$) were 81.5%, 12.4% and 1.2%, respectively.

General procedures for supporting an additive metal on a carrier (II)

In water (30 ml), $TlNO_3$ was dissolved. In a solution, were added formalin (0.2 g) and a pellet form palladium catalyst of 3.2 mm in diameter and 3.2 mm in height comprising 0.5% of palladium carried on $Al_2O_3$ (5 g) (Catalyst A'); a catalyst prepared by pulverizing said pellet form palladium catalyst to 60 mesh or lower (4 g) (Catalyst B'); a powdery catalyst comprising 2% of palladium carried on activated carbon (1.5 g) (Catalyst C'); or a powdery catalyst comprising 5% of palladium or ruthenium carried on $Al_2O_3$ (4 g) (Catalyst D'). All of the catalysts are commercially available from N. E. CHEMICAL CATALYST. Then, the mixture was aged at 50° C. for 2 to 3 hours. An amount of $TlNO_3$ is adjusted to obtain an intended molar ratio of Tl to the basic metal.

Then, water is removed by a rotary evaporator and the residue was dried in air at 100° C. for 12 hours.

Each of the catalysts prepared from Catalysts A', B', C' and D' is pretreated in a hydrogen stream at a temperature of 300° to 400° C. for 2 hours.

EXAMPLE 18

The Tl/Pd molar ratio was 4:1.

In a Hastelloy C made reactor tube having an inner diameter of 20 mm, Catalyst A' (4 g) modified with $TlNO_3$ as above was charged, and through the reactor tube, a mixture of R-113 and hydrogen in a molar ratio of 1:2 was flowed at a total flow rate of 21 ml/min. at 200° C.

A conversion was 7.3%, and selectivities of 3FCL and R-123a were 97.2% and 2.8%, respectively.

EXAMPLE 19

In the same manner as in Example 18 but keeping the reaction temperature at 250° C., the reaction was carried out.

A conversion was 8.5%, and selectivities of 3FCL and R-123a were 98.2% and 1.8%, respectively.

EXAMPLE 20

In the same manner as in Example 18 but keeping the reaction temperature at 280° C., the reaction was carried out.

After one hour of the reaction, the conversion was 19.5%, and selectivities of 3FCL, 3FH and R-123a were 96.1%, 2.2% and 1.7%, respectively. After five hours of the reaction, the conversion was 19.6%, and selectivities of 3FCL, 3FH and R-123a were 96.7%, 1.9% and 1.4%, respectively.

EXAMPLE 21

The Tl/Pd molar ratio was 4:1.

In a stainless steel tube reactor having an inner diameter of 7.2 mm, Catalyst B' (1.3 g) modified with $TlNO_3$ as above was charged, and through the reactor tube, a mixture of R-113 and hydrogen in a molar ratio of 1:2 was flowed at a total flow rate of 60 ml/min. at 250° C.

A conversion was 13.7%, and selectivities of 3FCL and 3FH were 96.4% and 3.6%, respectively.

EXAMPLE 22

In the same manner as in Example 21 but flowing the mixture of R-113 and hydrogen at a total flow rate of 27 ml/min., the reaction was carried out.

A conversion was 14.2%, and selectivities of 3FCL, 3FH and R-123a were 95.9%, 3.5% and 0.6%, respectively.

EXAMPLE 23

In the same manner as in Example 22 but using Catalyst D' modified with $TlNO_3$ in the Tl/Pd molar ratio of 1:1 (1.3 g), the reaction was carried out.

The conversion was 29.9%, and selectivities of 3FCL, 3FH and R-123a were 98.2%, 1.3% and 1.3%, respectively.

EXAMPLE 24

In the same manner as in Example 23 but adjusting the Tl/Pd molar ratio to 2:1, the reaction was carried out.

The conversion was 22.4%, and selectivities of 3FCL, 3FH and R-123a were 97.7%, 1.7% and 0.6%, respectively.

EXAMPLE 25

In the same manner as in Example 24 but keeping the reaction temperature at 340° C., the reaction was carried out.

The conversion was 46.5%, and selectivities of 3FCL, 3FH and R-123a were 95.7%, 3.9% and 0.5%, respectively.

EXAMPLE 26

In the same manner as in Example 23 but using Catalyst C' (5 g) modified with the said amount of $TlNO_3$, the reaction was carried out.

The conversion was 93.9%, and selectivities of 3FCL, 3FH and R-123a were 95.8%, 4.0% and 0.1%, respectively.

EXAMPLE 27

In the same manner as in Example 23 but using a mixture of R-113 and hydrogen in a molar ratio of 2:1, the reaction was carried out.

The conversion was 19.9%, and selectivities of 3FCL, 3FH and R-123a were 97.8%, 1.3% and 0.9%, respectively.

EXAMPLE 28

In the same manner as in Example 23 but using a mixture of R-113 and hydrogen in a molar ratio of 1:2.9, the reaction was carried out.

The conversion was 34.2% and selectivities of 3FCL, 3FH and R-123a were 97.8%, 1.3% and 0.6%, respectively.

EXAMPLE 29

In the same manner as in Example 21 but using a Catalyst C' (0.6 g) modified with the said amount of $TlNO_3$, the reaction was carried out.

The conversion was 17.1% and selectivities of 3FCL and 3FH were 92.8% and 7.2%, respectively.

EXAMPLE 30

In the same manner as in Example 23 but adjusting the Tl/Pd ratio to 0.5:1, the reaction was carried out.

The conversion was 57.2% and selectivities of 3FH, 3FCL, R-123a, R-134a, R-141a, R-160 and R-142 were 86.7%, 5.9%, 3.4%, 1.3%, 1.2%, 0.5% and 0.5%, respectively.

Comparative Example 6

In the same manner as in Example 21 without modification by thallium, the reaction was carried out.

The conversion was 64.3% and selectivities of R-143, R-141a, 3FH, R-123a, R-142 and R-160 were 40.2% 18.7%, 23.0%, 7.0%, 6.0%, and 4.6%, respectively.

Comparative Example 7

In the same manner as in Example 29 without modification by thallium, the reaction was carried out.

The conversion was 66.6%, and selectivities of R-143, 3FH, R-123a, R-141a, R-152a, R-160 and R-142 were 40.2%, 25.9%, 13.2%, 10.2%, 6.0%, 2.8% and 1.7%, respectively.

EXAMPLE 31

The Tl/Ru molar ratio was 2:1.

In a glass tube reactor having an inner diameter of 10 mm, Catalyst D') (1 g) comprising ruthenium as the base metal and modified with $TlNO_3$ as above was charged, and through the reactor tube, a mixture of R-113 and hydrogen in a molar ratio of 3:4 was flowed at a total flow rate of 35 ml/min. at 200° C.

A conversion was 10.4%, and selectivities of 3FCL and R-123a were 98.8% and 1.2%, respectively.

Comparative Example 8

In the same manner as in Example 31 without modification by thallium, the reaction was carried out.

The conversion was 64%, and selectivities of 3FCL, R-123a, 3FH and R-1132a were 66.7%, 28.6%, 4.2% and 1.8%, respectively.

What is claimed is:

1. A process for preparing 1-chloro-1,2,2-trifluoroethylene or 1,2,2-trifluoroethylene comprising reacting 1,1,2-trichloro-1,2,2-trifluoroethane and hydrogen in the presence of a catalyst which comprises at least one basic metal selected from the group consisting of palladium, rhodium and ruthenium and at least one additive metal selected from the group consisting of mercury, lead, cadmium, tin, indium, copper, bismuth, thallium and silver and a carrier selected from the group consisting of $Al_2O_3$, $SiO_2$ and activated carbon.

2. The process according to claim 1, wherein an amount of said basic metal selected from the group consisting of palladium, rhodium and ruthenium supported on the carrier is from 0.1 to 10% by weight.

3. The process according to claim 2, wherein said amount is from 0.5 to 5% by weight.

4. The process according to claim 1, wherein a molar ratio of hydrogen to 1,1,2-trichloro-1,2,2-trifluoroethane is from 0.5 to 4.0.

5. The process according to claim 4, wherein said ratio is from 0.5 to 3.5.

6. The process according to claim 1, wherein a molar ratio of said additive metal to said basic metal is from 0.01:1 to 10:1.

7. The process according to claim 6, wherein said molar ratio of said additive metal to said basic metal is from 0.2:1 to 4:1.

* * * * *